United States Patent
Ignatyev et al.

(10) Patent No.: US 9,163,039 B2
(45) Date of Patent: Oct. 20, 2015

(54) PROCESS FOR THE PREPARATION OF BIS(PERFLUOROALKYL)PHOSPHINIC ACID ANHYDRIDES

(75) Inventors: Nikolai (Mykola) Ignatyev, Duisburg (DE); Waldemar Wiebe, Cologne (DE); Helge Willner, Muehlheim/Ruhr (DE)

(73) Assignee: MERCK PATENT GMBH, Darmstadt (DE)

( * ) Notice: Subject to any disclaimer, the term of this patent is extended or adjusted under 35 U.S.C. 154(b) by 15 days.

(21) Appl. No.: 14/234,156

(22) PCT Filed: Jul. 6, 2012

(86) PCT No.: PCT/EP2012/002843
§ 371 (c)(1),
(2), (4) Date: Jan. 22, 2014

(87) PCT Pub. No.: WO2013/013766
PCT Pub. Date: Jan. 31, 2013

(65) Prior Publication Data
US 2014/0155649 A1 Jun. 5, 2014

(30) Foreign Application Priority Data

Jul. 25, 2011 (DE) .......................... 10 2011 108 324

(51) Int. Cl.
| | | |
|---|---|---|
| C07F 9/30 | (2006.01) | |
| B01D 53/28 | (2006.01) | |
| C07F 9/44 | (2006.01) | |
| C07F 9/53 | (2006.01) | |
| C07F 9/32 | (2006.01) | |
| C07F 9/34 | (2006.01) | |
| B01D 53/02 | (2006.01) | |
| B01D 53/26 | (2006.01) | |

(52) U.S. Cl.
CPC . *C07F 9/30* (2013.01); *B01D 53/28* (2013.01); *C07F 9/301* (2013.01); *C07F 9/308* (2013.01); *C07F 9/32* (2013.01); *C07F 9/3294* (2013.01); *C07F 9/34* (2013.01); *C07F 9/4492* (2013.01); *C07F 9/5337* (2013.01); *B01D 53/02* (2013.01); *B01D 53/261* (2013.01); *B01D 2251/61* (2013.01)

(58) Field of Classification Search
None
See application file for complete search history.

(56) References Cited

PUBLICATIONS

Mahmood et al., Inorg. Chem. 1986, 25, 3128-3131.*
International Search Report from PCT/EP2012/002843 dated Oct. 8, 2012.
R.C. Dobbie "The Reaction of Trifluoromethylphosphino-compounds with Nitric Oxide" J. Chem. Soc. (A), [1971], pp. 2894-2897.
Anton B. Burg "Bis(trifluoromethyl)phosphoryl-µ-oxo-bis(trifluoromethyl)phosphine. The Mixed Anhydride of a Phosphinous and Phosphinic Acid" Inorganic Chemistry, vol. 17, No. 8, [1978], pp. 2322-2324.
Tariq Mahmood et al. "New Perfiuoroalkylphosphonic and Bis(perfluoroalkyl)phosphinic Acids and Their Precursors" Inorg. Chem., vol. 25, [1986], pp. 3128-3131.
Rajendra P. Singh et al. "C6, C7, and C8 Perfluoroalkyl-Substituted Phosphinic Acids" Inorg. Chem., vol. 39, [2000], pp. 1787-1789.
Kurt Moedritzer "Synthesis and Properties of Phosphinic and Phosphonic Acid Anhydrides" J. of the American Chemical Society, vol. 83, [1961] pp. 4381-4384.
Gennady M. Kosolapoff, et al. "The Anhydrides of Dimethyl- and Diethyl-phosphinic Acids" J. of the American Chemical Society, vol. 73, [951] pp. 5466-5467.
Manfred Finke et al. "Preparation of simple phosphinic acid derivatives" Liebigs Ann. Chem., [1974], pp. 741-750. (English Translation 11 pages).

* cited by examiner

*Primary Examiner* — Karl J Puttlitz
(74) *Attorney, Agent, or Firm* — Miller, White, Zelano, Branigan, P.C.

(57) ABSTRACT

The invention relates to a process for the preparation of bis (perfluoroalkyl)phosphinic acid anhydrides by reaction of a bis(perfluoroalkyl)phosphinic acid with phosphorus pentoxide, to novel bis(perfluoroalkyl)phosphinic acid anhydrides and to uses of bis(perfluoroalkyl)phosphinic acid anhydrides.

19 Claims, No Drawings

PROCESS FOR THE PREPARATION OF BIS(PERFLUOROALKYL)PHOSPHINIC ACID ANHYDRIDES

The invention relates to a process for the preparation of bis(perfluoroalkyl)-phosphinic acid anhydrides by reaction of a bis(perfluoroalkyl)phosphinic acid with phosphorus pentoxide, to novel bis(perfluoroalkyl)phosphinic acid anhydrides and to uses of bis(perfluoroalkyl)phosphinic acid anhydrides.

R. C. Dobbie, J. Chem. Soc. (A), 1971, 2894-2897 reports on the synthesis of bis(trifluoromethyl)phosphinic acid anhydride by oxidation of $P_2(CF_3)_4$ (tetrakis-trifluoromethyldiphosphine) using 4 equivalents of NO in a sealed container at room temperature.

Anton B. Burg, Inorganic Chemistry, 1978, 17, 2322-2324 reports on the synthesis of bis(trifluoromethyl)phosphinic acid anhydride by reaction of bis-(trifluoromethyl)phosphinous acid anhydride $[(CF_3)_2POP(CF_3)_2]$ with bis-(trifluoromethyl)phosphinyl chloride.

T. Mahmood and J. M. Shreeve, Inorg. Chem. 1986, 25, 3128-3131 report on a synthesis of bis(pentafluoroethyl) phosphinic acid anhydride as non-volatile product remaining in the reaction vessel during the reaction, by reaction of chlorobis(pentafluoroethylphosphine) $[(C_2F_5)_2PCl]$ with an excess of $NO_2$ at 25° C. However, the NMR spectra in the literature reference indicated do not agree with the spectra of bis(pentafluoroethyl)phosphinic acid anhydride, a distillable liquid, which is obtained by the process according to the invention. The positions of the signals in the $^{19}F$ and $^{31}P$ NMR spectrum and their fine structure which are described in T. Mahmood and J. M. Shreeve in Inorg. Chem. 1986, 25, 3128-3131, are more similar to the corresponding spectra of bis (pentafluoroethyl)phosphinic acid. Spectra of bis(pentafluoroethyl)phosphinic acid are described, for example, in Example 3. The $CF_2$ group of bis(pentafluoroethyl)phosphinic acid $[(C_2F_5)_2P(O)OH]$ produces a simple doublet at −127.0 ppm with a coupling constant of $^2J_{P,F}=77$ Hz in the $^{19}F$ NMR spectrum in deuterated acetonitrile. The position of this signal is very similar to the signal described by T. Mahmood and J. M. Shreeve, namely $\delta CF_2 = -126.3$ and $^2J_{P,F}=73$ Hz in deuterated dimethyl sulfoxide.

The $^{19}F$ NMR spectrum of bis(pentafluoroethyl)phosphinic acid anhydride, as indicated in full in Example 1, is completely different. The fluorine atoms in the $CF_2$ groups in bis(pentafluoroethyl)phosphinic acid anhydride $[(C_2F_5)_2P(O)OP(O)(C_2F_5)_2]$ are not spectroscopically identical, but instead form a $CF_AF_B$ system, which results in two double doublets at −122.0 and −127.0 ppm (a so-called ABX spin system), with the coupling constants $^2J_{P,F(A)}=90$ Hz and $^2J_{P,F(B)}=107$ Hz. The $^{31}P$ NMR spectra of bis(pentafluoroethyl)phosphinic acid anhydride of Example 1 are likewise different compared with the anhydride, as described in T. Mahmood and J. M. Shreeve: Example 1 describes a complex multiplet, whereas the literature reference indicates a simple pentet. The accessibility of this compound from the reaction of this literature reference is therefore not given and this compound is therefore still novel.

Spectra of bis(pentafluoroethyl)phosphinic acid anhydride, as reported in Mahmood et al:
$^{19}F$: −81.4 s (CF3), −126.3 d ($J_{CF2-P}$) 73.24 Hz.
$^{31}P$: −0.3. pentet.

Rajendra P. Singh and J. M. Shreeve, Inorg. Chem. 2000, 39, 1787-1789 describe anhydrides of the formula $(R_F)_2P(O)OP(O)(R_F)_2$ where $R_F=C_6F_{13}$, $C_7F_{15}$ and $C_8F_{17}$ as intermediates in the preparation of the corresponding bis(perfluoroalkyl)phosphinic acids by oxidation of $(R_F)_2PI$ using $NO_2$. However, the anhydrides indicated as intermediate are not isolated, not analysed and no characterisation using physical-chemical methods is given. The accessibility of these compounds from the reaction of this literature reference is therefore likewise not given and these compounds are therefore still to be regarded as novel.

Anhydrides of carboxylic acids and alkylsulfonic acids are interesting reagents for organic syntheses. Bis(perfluoroalkyl)phosphinic acids and derivatives thereof are interesting components of proton-conducting membranes or are suitable, for example, as catalysts in organic chemistry. They are furthermore suitable for the synthesis of fluorine-containing surfactants or for further conversion into the corresponding acid chlorides, which are in turn suitable for the synthesis of novel materials, for example of ionic liquids.

The methods published to date for the preparation of bis (perfluoroalkyl)-phosphinic acid anhydrides, as described above, do not result in the desired products or cannot be used on an industrial scale. It is therefore desirable to have available a synthesis of these compounds which can be implemented economically and on an industrial scale in order that this interesting class of bis(perfluoroalkyl)phosphinic acid anhydrides and applications thereof can be investigated.

The object of the invention is therefore to develop an improved process for the preparation of bis(perfluoroalkyl) phosphinic acid anhydrides which meets the requirements of an industrial-scale economical synthesis.

Surprisingly, it has been found that bis(perfluoroalkyl) phosphinic acid can be reacted with phosphorus pentoxide and the desired anhydrides can be isolated therefrom.

K. Moedritzer, J. of the American Chemical Society, 1961, 83, 4381-4384 describes that phosphinic acid anhydrides cannot be prepared by dehydrogenation of the corresponding phosphinic acid.

G. M. Kosolapoff, R. M. Watson, J. of the American Chemical Society, 1951, 73, 5466-5467 describe a typical process for the preparation of unfluorinated dialkylphosphinic acid anhydrides based on the reaction of dialkylphosphinyl chlorides $[(Alk)_2P(O)Cl]$ with the corresponding dialkylphosphinic acids or esters thereof $[(Alk)_2P(O)OH$ or $(Alk)_2P(O)OR]$.

M. Fimke and H.-J. Kleiner, Liebigs Ann. Chem., 1974, 741-750, describe the dehydrogenation of unfluorinated dialkylphosphinic acids or salts or esters thereof with phosgene $(COCl_2)$ as dehydrogenating agent for the preparation of unfluorinated dialkylphosphinic acid anhydrides.

The invention therefore relates to a process for the preparation of bis(perfluoroalkyl)phosphinic acid anhydrides by reaction of a bis(perfluoroalkyl)phosphinic acid with phosphorus pentoxide.

Phosphorus pentoxide is taken to mean the chemical compound $P_2O_5$ or synonymously $P_4O_{10}$.

The compounds obtained in accordance with the invention are volatile and can be separated from the reaction mixture and optionally purified by distillation.

Bis(perfluoroalkyl)phosphinic acid anhydrides of the formula I

   I where
x denotes 1, 2, 3, 4, 5, 6, 7, 8, 9, 10, 11 or 12
are preferably prepared.

These are symmetrical acid anhydrides.

The starting compounds, i.e. the bis(perfluoroalkyl)phosphinic acid, in particular bis(perfluoroalkyl)phosphinic acids of the formula II

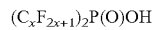   II where x denotes 1, 2, 3, 4, 5, 6, 7, 8, 9, 10, 11 or 12, is/are commercially available or can be prepared by standard synthetic methods, for example by the methods as described in the published specifications WO 03/087110 or WO 2010/012359.

Particular preference is given to the preparation of compounds of the formula I in which x stands for 2, 3, 4 or 5, very particularly preferably x stands for 2 or 4.

The process, as described above, is carried out at temperatures of 20° to 250° C., preferably at temperatures of 60° to 210° C. The reactivity of the corresponding bis(perfluoroalkyl)phosphinic acid should be taken into account here. As specifically explained in the experimental part, the preparation of bis(nonafluorobutyl)phosphinic acid anhydride is carried out at 60° C. in an inert solvent (1,1,1,3,3-pentafluorobutane), whereas bis(pentafluoroethyl)phosphinic acid anhydride is prepared at 210° C. without the use of solvents. The precise reaction temperature is at the discretion of the person skilled in the art working in the area of organic synthesis.

The process can be carried out without a solvent or in the presence of solvents. Suitable solvents are, for example, fluoroalkanes, chloroalkanes or fluorochloroalkanes, in particular 1,1,1,3,3-pentafluorobutane or 1,1,2-trichlorotrifluoroethane. The reaction is preferably carried out without solvents or in the solvent 1,1,1,3,3-pentafluorobutane.

The reaction of the bis(perfluoroalkyl)phosphinic acid with phosphorus pentoxide can be carried out without protective-gas atmosphere. However, the reaction is preferably carried out under dried air or in an inert-gas atmosphere.

The invention furthermore relates to the bis(perfluoroalkyl)phosphinic acid anhydrides of the formula I

   I where x denotes 2, 3, 4, 5, 6, 7, 8, 9, 10, 11 or 12.

x preferably stands for 3, 4, 5, 6, 7, 8, 9, 10, 11 or 12, particularly preferably for 2, 3, 4, 5, 6, 7 or 8, very particularly preferably for 2, 3, 4 or 5 or very particularly preferably for 3, 4, 6 or 12. In particular, x preferably stands for 2 and 4, very particularly preferably for 4.

The bis(perfluoroalkylphosphinic) acid anhydrides which can be prepared or are prepared by the process according to the invention, preferably the compounds of the formula I, as described above, where x denote 1, 2, 3, 4, 5, 6, 7, 8, 9, 10, 11 or 12, are particularly suitable as dehydrating agent or as drying agent.

Furthermore, the bis(perfluoroalkyl)phosphinic acid anhydrides which can be prepared or are prepared by the process according to the invention, preferably the compounds of the formula I, as described above, where x denote 1, 2, 3, 4, 5, 6, 7, 8, 9, 10, 11 or 12, are ideal starting compounds for the preparation of other derivatives of the parent bis(perfluoroalkyl)phosphinic acid or of salts having the corresponding bis(perfluoroalkyl)phosphinate anion.

Preferred bis(perfluoroalkyl)phosphinic acid derivatives are, for example, bis(perfluoroalkyl)phosphinyl chlorides, in particular of the formula III

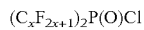   III, where x denotes 1, 2, 3, 4, 5, 6, 7, 8, 9, 10, 11 or 12, bis(perfluoroalkyl)phosphinyl bromides, in particular of the formula IV

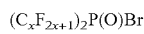   IV, where x denotes 1, 2, 3, 4, 5, 6, 7, 8, 9, 10, 11 or 12, bis(perfluoroalkyl)phosphinic acid trialkylsilyl ethers, in particular of the formula V

   V, where x denotes 1, 2, 3, 4, 5, 6, 7, 8, 9, 10, 11 or 12 and alkyl denotes a straight-chain or branched alkyl group having 1 to 4 C atoms, N,N-dialkylbis(perfluoroalkyl)phosphinylamines or -amides, in particular of the formula VI,

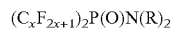   VI, where x denotes 1, 2, 3, 4, 5, 6, 7, 8, 9, 10, 11 or 12 and

R in each case, independently of one another, denotes H or a straight-chain or branched alkyl group having 1 to 12 C atoms, bis(perfluoroalkyl)phosphinyl cyanides, in particular of the formula VII

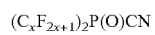   VII, where x denotes 1, 2, 3, 4, 5, 6, 7, 8, 9, 10, 11 or 12 or bis(perfluoroalkyl)phosphinyl isothiocyanates, in particular of the formula VIII

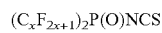   VIII, where x denotes 1, 2, 3, 4, 5, 6, 7, 8, 9, 10, 11 or 12.

The reaction conditions in these further derivatisations are adequately known to the person skilled in the art. Working examples are described in the examples.

A straight-chain (or synonymously linear) or branched alkyl group having 1 to 4 C atoms is, for example, methyl, ethyl, n-propyl, isopropyl, n-butyl, sec-butyl or tert-butyl. A linear or branched alkyl group having 1 to 12 C atoms includes the embodiments of the linear or branched alkyl group having 1 to 4 C atoms and, for example, n-pentyl, n-hexyl, n-heptyl, n-octyl, ethylhexyl, n-nonyl, n-decyl, n-undecyl or n-dodecyl.

As a further product besides the derivatives described above, in particular the compounds of the formula III to VIII, the derivatisation generally likewise gives the corresponding bis(perfluoroalkyl)phosphinates, where the cation here may be either inorganic or organic.

In particular, the derivatisation gives compounds of the formula IX

   IX, where x denotes 1, 2, 3, 4, 5, 6, 7, 8, 9, 10, 11 or 12 and Kt is an inorganic or organic cation.

The organic cation for Kt is, for example, selected from ammonium cations, sulfonium cations, phosphonium cations, uronium cations, thiouronium cations, guanidinium cations or heterocyclic cations.

Inorganic cations for Kt are, for example, selected from metal cation from groups 1 to 12 of the Periodic Table, selected from alkali-metal cations, $Ag^+$, $Mg^{2+}$, $Cu^+$, $Cu^{2+}$, $Zn^{2+}$, $Ca^{2+}$, $Y^{+3}$, $Yb^{+3}$, $La^{+3}$, $Sc^{+3}$, $Ce^{+3}$, $Nd^{+3}$, $Tb^{+3}$, $Sm^{+3}$ or complex (ligand-containing) metal cations, which contain rare-earth metals, transition metals or noble metals, such as rhodium, ruthenium, iridium, palladium, platinum, osmium, cobalt, nickel, iron, chromium, molybdenum, tungsten, vanadium, titanium, zirconium, hafnium, thorium, uranium, gold.

The following working examples are intended to explain the invention without limiting it. The invention can be carried out correspondingly throughout the range claimed. Starting from the examples, possible variants can also be derived. In particular, the features and conditions of the reactions described in the examples can also be applied to other reactions which are not described in detail, but fall within the scope of protection of the claims.

EXAMPLES

The substances obtained are characterised by means of Raman spectroscopy, elemental analysis and NMR spectroscopy. The NMR spectra are measured on solutions in deuterated acetone-$D_6$ on a Bruker Avance III spectrometer with deuterium lock. The measurement frequencies of the various nuclei are: $^1$H: 400.17 MHz, $^{19}$F: 376.54 MHz, $^{11}$B: 128.39 MHz, $^{31}$P: 161.99 MHz and $^{13}$C: 100.61 MHz. The referencing is carried out with an external reference: TMS for $^1$H and $^{13}$C spectra; $CCl_3F$— for $^{19}$F and $BF_3.Et_2O$— for $^{11}$B spectra.

Example 1

Bis(pentafluoroethyl)phosphinic acid anhydride 8.8 g (29.1 mmol) of bis(pentafluoroethyl)phosphinic acid, $(C_2F_5)_2P(O)OH$, are added to 16.8 g (118 mmol) of phosphorus pentoxide, $P_2O_5$, and the mixture is heated under reflux at 210° C. (temperature in oil bath) for 6 hours. A clear colourless liquid is subsequently distilled off in a reduced vacuum (P=100 mbar). Boiling point: 78° C. (100 mbar). The yield of bis(pentafluoroethyl)phosphinic acid anhydride, $(C_2F_5)_2(O)POP(O)(C_2F_5)_2$, is 7.2 g (84%), based on the bis(pentafluoroethyl)phosphinic acid employed. NMR data: external lock: acetone-$D_6$; reference substance: for $^1$H and $^{13}$C spectra-TMS, for $^{19}$F spectra-$CCl_3F$ and for $^{31}$P spectra-85% $H_3PO_4$ in $D_2O$):

$^{31}$P NMR spectrum, δ, ppm: 3.2 m.

$^{19}$F NMR spectrum, δ, ppm: −83.2 s (12F, 4$CF_3$); −122.0 d,d (4$F_A$, $CF_2$), $^2J_{P,F(A)}$=90 Hz, $^2J_{F(A),F(B)}$=340 Hz; −127.0 d,d (4$F_B$, $CF_2$), $^2J_{P,F(B)}$=107 Hz, $^2J_{FA,FB}$=340 Hz.

$^{13}$C NMR spectrum, δ, ppm: 111.3 t,d,q (4C, 4$CF_2$), $^1J_{F,C}$=286 Hz, $^1J_{P,C}$=150 Hz, $^2J_{F,C}$=43 Hz; 117.9 q,t,d (4C, 4$CF_3$), $^1J_{F,C}$=286 Hz, $^2J_{F,C}$=30 Hz, $^2J_{P,C}$=23 Hz.

Raman spectrum for $(C_2F_5)_2P(O)OP(O)(C_2F_5)_2$, ṽ, cm$^{-1}$: 1356 s, 1224 m, 1166 m, 759 vs, 700 m, 638 s, 597, 541, 370 m, 280 s, 260 s, 253 s, 151 s. IR$_{(ATR)}$ for $(C_2F_5)_2P(O)OP(O)(C_2F_5)_2$, ṽ, cm$^{-1}$: 1354 w, 1339 w, 1305 s, 1219 vs, 1148 vs, 1001 s, 932 s, 760 m, 753 m, 628 m, 598 m, 567 m, 507 s, 468 w, 415 w.

Example 2

Bis(nonafluorobutyl)phosphinic acid anhydride 7.0 g (14.0 mmol) of bis(perfluorobutyl)phosphinic acid, $(C_4F_9)_2P(O)OH$, are dissolved in 25 ml of 1,1,1,3,3-pentafluorobutane, 7.9 g (55.7 mmol) of phosphorus pentoxide, $P_2O_5$, are added, and the mixture is heated under reflux for 60° C. for 4 days. After fractional distillation, 3.3 g of bis (perfluoro-butyl)phosphinic acid anhydride are obtained as a clear colourless liquid. This corresponds to a yield of 48%, based on the bis(nonafluorobutyl)phosphinic acid employed. Boiling point: 77° C. (0.6 mbar).

NMR data: external lock: $D_2O$; reference substance: for $^1$H and $^{13}$C spectra-TMS, for $^{19}$F spectra-$CCl_3F$ and for $^{31}$P spectra-85% $H_3PO_4$ in $D_2O$):

$^{31}$P NMR spectrum, δ, ppm: 2.4 m.

$^{19}$F NMR spectrum, δ, ppm: −83.3 s (12F, 4$CF_3$); −115.8 d,d (4$F_A$, $CF_2$) $^2J_{P,F(A)}$=88 Hz, $^2J_{F(A),F(B)}$=337 Hz; −119.7 d,d (4$F_B$, $CF_2$), $^2J_{P,F(B)}$=107 Hz; −120.6 m (8F, 4$CF_2$); −127.6 s (8F, 4$CF_2$).

Example 3

Hydrolysis of bis(pentafluoroethyl)phosphinic acid anhydride $(C_2F_5)_2(O)POP(O)(C_2F_5)_2 + H_2O \rightarrow 2(C_2F_5)_2P(O)OH$ 0.19 g (10.5 mmol) of water is added to 5.90 g (10.0 mmol) of bis(penta-fluoroethyl)phosphinic acid anhydride, $(C_2F_5)_2(O)POP(O)(C_2F_5)_2$, at 0° C. with vigorous stirring. 6.09 g of a clear colourless liquid are obtained. The yield of bis(pentafluoroethyl)phosphinic acid is quantitative.

NMR data (solvent/lock: $CD_3CN$; reference substance: $^{19}$F $CCl_3F$, $^{31}$P 85% $H_3PO_4$):

$^{19}$F NMR spectrum, δ, ppm: −82.1 s (6F, 2$CF_3$); −127.0 d (4F, 2$CF_2$), $^2J_{P,F}$=77 Hz.

$^{31}$P NMR spectrum, δ, ppm: −0.1 quin, $^2J_{P,F}$=76 Hz.

Example 4

Preparation of bis(pentafluoroethyl)phosphinyl chloride

A:

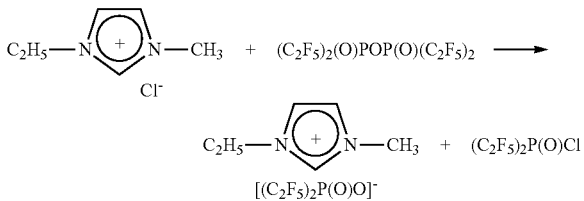

6.1 g (10.4 mmol) of bis(pentafluoroethyl)phosphinic acid anhydride, $(C_2F_5)_2(O)POP(O)(C_2F_5)_2$, are added to 2.5 g (12.3 mmol) of 1-butyl-3-methylimidazolium chloride, EMIM Cl, and the mixture is stirred at room temperature for 15 minutes. After subsequent distillation (boiling point: 86° C.), 2.9 g of bis(pentafluoroethyl)phosphinyl chloride, $(C_2F_5)_2P(O)Cl$, are obtained, which corresponds to a yield of 88%.

Bis(pentafluoroethyl)phosphinyl chloride:
$^{31}$P NMR spectrum (solvent: $CD_3CN$; reference substance: 85% $H_3PO_4$), δ, ppm: 21.6 t,t; $^2J_{P,F}$=95 Hz, $^2J_{P,F}$=98 Hz;
$^{19}$F NMR spectrum (solvent: $CD_3CN$; reference substance: $CCl_3F$), δ, ppm: −79.8 s (6F, 2$CF_3$); −118.2 d,d (2$F_A$, $CF_2$), $^2J_{P,F(A)}$=92 Hz, $^2J_{F(A),F(B)}$=326 Hz; −122.4 d,d (2$F_B$, $CF_2$), $^2J_{P,F(B)}$=100 Hz, $^2J_{F(A),F(B)}$=325 Hz.

B:

11.1 g (18.9 mmol) of bis(pentafluoroethyl)phosphinic acid anhydride, $(C_2F_5)_2(O)POP(O)(C_2F_5)_2$, are added to 1.98 g (18.1 mmol) of tetramethyl-ammonium chloride. The reaction mixture is stirred under reflux at 190° C. (temperature in oil bath) for 2 hours. 5.73 g of bis(pentafluoroethyl)phosphinyl chloride, $(C_2F_5)_2P(O)Cl$, formed is then condensed off, which corresponds to a yield of 99%.

Example 5

Preparation of bis(pentafluoroethyl)phosphinyl bromide

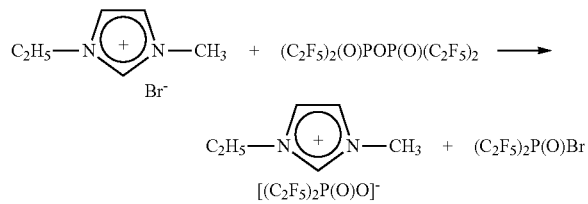

10.2 g (17.4 mmol) of bis(pentafluoroethyl)phosphinic acid anhydride, $(C_2F_5)2(O)POP(O)(C_2F_5)_2$, are added to 3.2 g (16.7 mmol) of 1-ethyl-3-methylimidazolium bromide, and the mixture is stirred at room temperature for 10 minutes. The mixture is subsequently heated under reflux for 5 minutes in order to complete the reaction. After subsequent distillation (boiling point: 97° C.), 5.3 g of bis(pentafluoroethyl)phosphinyl bromide, $(C_2F_5)_2P(O)Br$, are obtained, which corresponds to a yield of 87%.

NMR data of bis(pentafluoroethyl)phosphinyl bromide (external lock: $D_2O$; reference substance for $^{19}F$ NMR spectrum—$CCl_3F$, for $^{31}P$ NMR spectra—85% $H_3PO_4$):

$^{31}P$ NMR spectrum, δ, ppm: 15.2 quin; $^2J_{P,F}=94$ Hz.

$^{19}F$ NMR spectrum, δ, ppm: −80.6 s (6F, $2CF_3$); −117.4 d,d (2F, $CF_2$), $^2J_{P,F(A)}=93$ Hz, $^2J_{F(A),F(B)}=322$ Hz; −122.8 d,d ($2F_B$, $CF_2$), $^2J_{P,F(B)}=96$ Hz, $^2J_{F(A),F(B)}=322$ Hz.

Example 6

Preparation of bis(pentafluoroethyl)phosphinic acid trimethylsilyl ether

A:

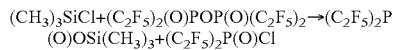

$(CH_3)_3SiCl+(C_2F_5)_2(O)POP(O)(C_2F_5)_2 \rightarrow (C_2F_5)_2P(O)OSi(CH_3)_3+(C_2F_5)_2P(O)Cl$ 4.91 g (45 mmol) of trimethylchlorosilane are added to 4.72 g (8 mmol) of bis(pentafluoroethyl)phosphinic acid anhydride, $(C_2F_5)_2(O)POP(O)(C_2F_5)_2$, at room temperature, the mixture is stirred for 10 min and subsequently subjected to fractional distillation. 2.13 g of bis(pentafluoroethyl)phosphinyl chloride and 2.81 g of bis(pentafluoroethyl)phosphinic acid trimethylsilyl ether are obtained. This corresponds to a yield of 83 and 93% respectively.

Bis(peentafluoroethyl)phosphinic acid trimethylsilyl ether:

$^{31}P$ NMR spectrum (solvent: $CD_3CN$; reference substance: 85% $H_3PO_4$), δ, ppm: −2.7 br.m;

$^{19}F$ NMR spectrum (solvent: $CD_3CN$; reference substance: $CCl_3F$), δ, ppm: −81.1 br. s (6F, $2CF_3$); −125.4 br.m (4F, $2CF_2$) $^1H$ NMR spectrum (solvent: $CD_3CN$; reference substance: TMS), δ, ppm: 0.45 br.s (9H, $3CH_3$).

B:

$(CH_3)_3SiOSi(CH_3)_3+(C_2F_5)^2(O)POP(O)(C_2F_5)^2 \rightarrow 2(C_2F_5)_2P(O)OSi(CH_3)_3$ 7.7 g (47.4 mmol) of hexamethyldisiloxane, $(CH_3)_3SiOSi(CH_3)_3$, are added to 14.4 g (24.6 mmol) of bis(pentafluoroethyl)phosphinic acid anhydride, $(C_2F_5)2(O)POP(O)(C_2F_5)_2$, and the mixture is stirred at room temperature for 20 minutes. After fractional distillation in vacuo (P=8 mbar), 15.0 g of bis-(pentafluoroethyl)phosphinic acid trimethylsilyl ether are obtained, which corresponds to a yield of 81%. Boiling point: 58° C. (8 mbar).

Example 7

Preparation of N,N-dibutylbis(pentafluoroethyl)phosphinylamide 0.58 g (4.5 mmol) of dibutylamine, $(C_4H_9)_2NH$, is slowly added to 1.21 g (2.1 mmol) of bis(pentafluoroethyl)phosphinic acid anhydride, $(C_2F_5)_2(O)POP(O)-(C_2F_5)_2$, at 0° C., and the mixture is stirred for 15 minutes. After subsequent vacuum distillation, 0.65 g of N,N-dibutylbis(pentafluoroethyl)phosphinylamides, $(C_2F_5)_2P(O)N(C_4H_9)_2$ are obtained, which corresponds to a yield of 76%.

$^{31}P$ NMR spectrum (solvent: $CD_3CN$; reference substance: 85% $H_3PO_4$), δ, ppm:

13.0 quin,quin; $^2J_{P,F}=76$ Hz, $^3J_{P,H}=11$ Hz.

$^{19}F$ NMR spectrum (solvent: $CD_3CN$; reference substance: $CCl_3F$), δ, ppm: −81.4 s (6F, $2CF_3$); −122.3 d (4F, $2CF_2$), $^2J_{P,F}=75$ Hz.

$^1H$ NMR spectrum (solvent: $CD_3CN$; reference substance: TMS), δ, ppm: 0.93 t (6H, $^2CH_3$), $^3J_{H,H}=7$ Hz; 1.30 d,q (4H, $2CH_2$), $^3J_{H,H}=7$ Hz; 1.59 m (4H, $2CH_2$); 3.21 m (4H, $2CH_2$).

Example 8

Preparation of bis(pentafluoroethyl)phosphinyl cyanide

A:

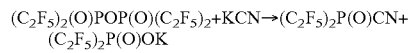

$(C_2F_5)_2(O)POP(O)(C_2F_5)_2+KCN \rightarrow (C_2F_5)_2P(O)CN+(C_2F_5)_2P(O)OK$ 0.78 g (12.0 mmol) of finely ground potassium cyanide are initially introduced in 24.4 g of sulfolane and stirred at 90° C. for one hour in vacuo and freed from volatile constituents. After the reaction mixture has been cooled to 40° C., 6.68 g (11.4 mmol) of bis(pentafluoroethyl)phosphinic acid anhydride, $(C_2F_5)2(O)POP(O)(C_2F_5)_2$, are added, the mixture is warmed to 55° C. and stirred for a further 3.5 hours. 3.15 g of a mixture consisting of bis(penta-fluoroethyl)phosphinic acid anhydride and bis(pentafluoroethyl)phosphinyl cyanide, $(C_2F_5)_2P(O)CN$, in the molar ratio 1:9 are subsequently condensed off. After fractional distillation of this mixture, 2.1 g of bis(pentafluoroethyl)phosphinyl cyanide having a boiling point of 72° C. are obtained. This corresponds to a yield of 59% (based on the anhydride).

NMR data of bis(pentafluoroethyl)phosphinyl cyanide (external lock: $D_2O$; reference substance for $^{19}F$ NMR spectrum-$CCl_3F$, for $^{31}P$ NMR spectrum-85% $H_3PO_4$):

$^{31}P$ NMR spectrum, δ, ppm: −13.9 t,t; $^2J_{P,F}=90$ Hz, $^2J_{P,F}=101$ Hz.

$^{19}F$ NMR spectrum, δ, ppm: −81.0 s (6F, $2CF_3$); −119.1 d,d (2F, $CF_2$), $^2J_{P,F(A)}=90$ Hz, $^2J_{F(A),F(B)}=333$ Hz; −125.6 d,d ($2F_B$, $CF_2$), $^2J_{P,F(B)}=101$ Hz, $^2J_{F(A),F(B)}=333$ Hz.

Raman spectrum for $(C_2F_5)_2P(O)CN$, ṽ, $cm^{-1}$: 2204 vs, 1337 s, 1300 s, 1226 m, 1133 m, 995 w, 757 vs, 672 w, 634 m, 592 w, 542 w, 468 w, 369 m, 328 m, 281 s, 257 s, 198 w, 144 s, 109 s.

$IR_{(ATR)}$ for $(C_2F_5)_2P(O)CN$, ṽ, $cm^{-1}$: 2202 s, 1354 w, 1295 vs, 1218 vs, 1143 vs, 993 s, 758 vs, 713 m, 674 s, 564 s, 506 s, 490 s, 423 w.

B:

0.97 g (14.9 mmol) of finely ground potassium cyanide are initially introduced in 19.4 g of sulfolane and stirred at 60° C. overnight in vacuo and freed from volatile constituents. After the reaction mixture has been cooled to 30° C., 12.43 g (21.2 mmol) of bis(pentafluoroethyl)phosphinic acid anhydride, $(C_2F_5)2(O)POP(O)(C_2F_5)_2$, are added, and the mixture is stirred at this temperature for 24 hours. The volatile constituents are subsequently condensed in vacuo into a flask cooled to −196° C. 7.7 g of the condensed-off mixture, which consists of bis(pentafluoroethyl)phosphinic acid anhydride and bis(pentafluoroethyl)phosphinyl cyanide in the molar ratio 2:3, are warmed to—40° C., and 3.4 g of bis(pentafluoroethyl)phosphinyl cyanide, $(C_2F_5)_2P(O)CN$, are condensed over into a receiver cooled to—196° C. in vacuo. This corresponds to a yield of 73% (based on the potassium cyanide employed).

Example 9

Preparation of bis(pentafluoroethyl)phosphinyl isothiocyanate $(C_2F_5)_2(O)POP(O)(C_2F_5)_2 + KSCN \rightarrow (C_2F_5)_2P(O)NCS + (C_2F_5)_2P(O)OK$ 1.02 g (10.5 mmol) of finely ground potassium thiocyanate, KSCN, are initially introduced in 19.6 g of sulfolane, stirred and freed from volatile constituents at 40° C. overnight in vacuo. After the solution has been cooled to 40° C., 6.38 g (11.4 mmol) of bis(pentafluoroethyl)phosphinic acid anhydride, $(C_2F_5)2(O)POP(O)(C_2F_5)_2$, are added, and the mixture is stirred at 70° C. for one hour. After volatile components have been condensed off into a flask cooled to—196° C. and subsequent fractional distillation, 3.39 g of a clear colourless liquid—bis(pentafluoroethyl)phosphinyl isothiocyanate having a boiling point of 120° C. are obtained. This corresponds to a yield of 94% (based on the anhydride employed).

NMR data of bis(pentafluoroethyl)phosphinyl cyanide (external lock: $D_2O$; reference substance for $^{19}F$ NMR spectrum—$CCl_3F$, for $^{31}P$ NMR spectrum—85% $H_3PO_4$):

$^{31}P$ NMR spectrum, δ, ppm: −12.2 t,t; $^2J_{P,F}$=99 Hz, $^2J_{P,F}$=84 Hz.

$^{19}F$ NMR spectrum, δ, ppm: −81.7 s (6F, $2CF_3$); −122.1 d,d (2F, $CF_2$), $^2J_{P,FA}$=85 Hz, $^2J_{FA,FB}$=334 Hz; −126.0 d,d ($2F_B$, $CF_2$), $^2J_{P,FB}$=100 Hz, $^2J_{FA,FB}$=332 Hz. Raman spectrum for $(C_2F_5)_2P(O)NCS$, ṽ, cm$^{-1}$: 1971 vw, 1332 s, 1303 s, 1227 m, 1156 m, 1088 m, 983 w, 755 vs, 655 w, 634 m, 541 w, 442 w, 414 s, 366 m, 330 m, 265 s, 163 m, 144 m.

IR $_{(ATR)}$ for $(C_2F_5)_2P(O)NCS$, ṽ, cm$^{-1}$: 1946 vs, 1294 s, 1217 vs, 1148 vs, 995 m, 928 m, 758 m, 622 w, 596 w, 562 m, 499 s.

The invention claimed is:

1. A process for preparation of a bis(perfluoroalkyl)phosphinic acid anhydride comprising:

reacting a bis(perfluoroalkyl)phosphinic acid with phosphorus pentoxide.

2. The process according to claim 1, wherein said bis(perfluoroalkyl)phosphinic acid is of formula II $(C_xF_{2x+1})_2P(O)OH$   II, where x denotes 1, 2, 3, 4, 5, 6, 7, 8, 9, 10, 11 or 12.

3. The process according to claim 1, wherein the reaction is carried out at temperatures of 20° to 250° C.

4. A compound of formula I $(C_xF_{2x+1})_2(O)POP(O)(C_xF_{2x+1})_2$   I where x denotes 3, 4, 5, 6, 7, 8, 9, 10, 11 or 12.

5. A dehydrating agent or desiccant comprising a compound of formula I $(C_xF_{2x+1})_2(O)POP(O)(C_xF_{2x+1})_2$   I where x denotes 1, 3, 4, 5, 6, 7, 8, 9, 10, 11 or 12, as a dehydrating agent or as desiccant.

6. The process according to claim 2, wherein the reaction is carried out at temperatures of 20° to 250° C.

7. The process according to claim 1, wherein said bis(perfluoroalkyl)phosphinic acid anhydride is of formula I $(C_xF_{2x+1})_2(O)POP(O)(C_xF_{2x+1})_2$   I where x denotes 1, 2, 3, 4, 5, 6, 7, 8, 9, 10, 11 or 12.

8. The process according to claim 2, wherein x is 2, 3, 4 or 5.

9. The process according to claim 2, wherein x is 2 or 4.

10. The process according to claim 1, wherein the reaction is carried out at temperatures of 60° to 210° C.

11. The process according to claim 2, wherein the reaction is carried out at temperatures of 60° to 210° C.

12. The process according to claim 1, wherein the reaction is carried out without a solvent.

13. The process according to claim 1, wherein the reaction is carried out in the presence of a solvent selected from fluoroalkanes, chloroalkanes and fluorochloroalkanes.

14. The process according to claim 1, wherein the reaction is carried out in the presence of a solvent selected from 1,1,1,3,3-pentafluorobutane and 1,1,2-trichlorotrifluoroethane.

15. The process according to claim 1, wherein the reaction is carried under dried air or in an inert-gas atmosphere.

16. A compound according to claim 4, wherein x is 3, 4, 5, 6, 7 or 8.

17. A compound according to claim 4, wherein x is 3, 4 or 5.

18. A compound according to claim 4, wherein x is 3, 4, 6 or 12.

19. A compound according to claim 4, wherein x is 4.

* * * * *